US012692196B2

(12) United States Patent
Matsuura

(10) Patent No.: US 12,692,196 B2
(45) Date of Patent: Jul. 28, 2026

(54) METHOD FOR PRODUCING ZIRCONIA SINTERED BODY

(71) Applicant: Kuraray Noritake Dental Inc., Kurashiki (JP)

(72) Inventor: Atsushi Matsuura, Aichi (JP)

(73) Assignee: Kuraray Noritake Dental Inc., Kurashiki (JP)

( * ) Notice: Subject to any disclaimer, the term of this patent is extended or adjusted under 35 U.S.C. 154(b) by 603 days.

(21) Appl. No.: 18/027,680

(22) PCT Filed: Sep. 24, 2021

(86) PCT No.: PCT/JP2021/035176
§ 371 (c)(1),
(2) Date: Mar. 22, 2023

(87) PCT Pub. No.: WO2022/065452
PCT Pub. Date: Mar. 31, 2022

(65) Prior Publication Data
US 2023/0382808 A1       Nov. 30, 2023

(30) Foreign Application Priority Data
Sep. 25, 2020     (JP) ................................. 2020-161531

(51) Int. Cl.
*A61K 6/818*       (2020.01)
*C04B 35/48*       (2006.01)

(52) U.S. Cl.
CPC .............. *C04B 35/48* (2013.01); *A61K 6/818* (2020.01); *C04B 2235/3225* (2013.01); *C04B 2235/6562* (2013.01); *C04B 2235/6567* (2013.01)

(58) Field of Classification Search
CPC ...... C04B 2235/6576; C04B 2235/661; C04B 2235/75; C04B 2235/80; C04B 2235/96;
(Continued)

(56) References Cited

U.S. PATENT DOCUMENTS

2015/0247672 A1     9/2015   Schmidt et al.
2018/0002235 A1     1/2018   Ito et al.
(Continued)

FOREIGN PATENT DOCUMENTS

CN        110204333 A       9/2019
JP        2015531048 A      10/2015
(Continued)

OTHER PUBLICATIONS

WO2019131782A1 , English Translation Description, Kato et al. "Zirconia Semi-Sintered Body Suitable for Dental Use", Espacenet Sep. 25, 2025, Jul. 4, 2019, Year 2019 (Year: 2019).*
(Continued)

*Primary Examiner* — Alison L Hindenlang
*Assistant Examiner* — Christopher Paul Daigler
(74) *Attorney, Agent, or Firm* — Element IP, PLC

(57)                 ABSTRACT
The present invention provides a method of production of a zirconia sintered body by which a zirconia molded body or zirconia pre-sintered body having a plurality of layers containing different amounts of stabilizer is sintered in a short time period to produce a zirconia sintered body having hardly noticeable stripes between layers differing in yttria content. The present invention relates to a method for producing a zirconia sintered body, comprising a firing step of firing a zirconia molded body or a zirconia pre-sintered body,
    the zirconia molded body or the zirconia pre-sintered body comprising a plurality of layers containing a stabilizer,
    the plurality of layers including layers having different stabilizer contents,
    the firing step comprising at least three stages of temperature-increasing process including a first temperature-increasing step (H1), a second temperature-increasing step (H2), and a third temperature-increasing step (H3),
(Continued)

the method satisfying HR2=more than 0° C./min and less than 50° C./min, HR3=5 to 150° C./min, and HR3/HR2>1, where HR2 is a rate of temperature increase in H2, and HR3 is a rate of temperature increase in H3, the temperature-increasing process having start temperatures that are 1,000° C. or less in H1, more than 1,250° C. and 1,450° C. or less in H2, and 1,450° C. or more and 1,550° C. or less in H3, the temperature-increasing process having end temperatures that are more than 1,250° C. and 1,450° C. or less in H1, 1,450° C. or more and 1,550° C. or less in H2, and 1,500° C. or more and 1,750° C. or less in H3.

15 Claims, 1 Drawing Sheet

(58) Field of Classification Search
CPC .... C04B 2235/9653; C04B 2235/9661; C04B 2235/6565; C04B 2235/6562; C04B 2235/3225; C04B 2237/348; C04B 2237/58; C04B 35/64; C04B 35/48
See application file for complete search history.

(56) References Cited

U.S. PATENT DOCUMENTS

| | | | |
|---|---|---|---|
| 2018/0125616 A1 | 5/2018 | Kitamura et al. | |
| 2019/0127284 A1* | 5/2019 | Balasubramanian | ....................... A61C 13/0022 |
| 2019/0328622 A1 | 10/2019 | Bäurer | |

| | | | |
|---|---|---|---|
| 2019/0380815 A1 | 12/2019 | Aiba et al. |
| 2019/0381769 A1 | 12/2019 | Reinshagen et al. |
| 2020/0113658 A1 | 4/2020 | Ban et al. |
| 2022/0017423 A1 | 1/2022 | Kato et al. |
| 2022/0267215 A1 | 8/2022 | Sakamoto et al. |

FOREIGN PATENT DOCUMENTS

| | | | |
|---|---|---|---|
| JP | 2017128466 A | | 7/2017 |
| JP | 2018080160 A | | 5/2018 |
| JP | WO2019131782 A1 | * | 7/2019 |
| JP | 2019163246 A | | 9/2019 |
| JP | 2019524298 A | | 9/2019 |
| JP | 2020075858 A | | 5/2020 |
| WO | WO-2016104724 A1 | | 6/2016 |
| WO | WO-2018155459 A1 | | 8/2018 |
| WO | WO-2020138316 A1 | | 7/2020 |
| WO | WO-2021020582 A1 | | 2/2021 |

OTHER PUBLICATIONS

Cn11020204333a, English Translation Description, Lou et al. Processing Technology Capable of Rapidly Preparing Multi-Layer Zirconia Ceramic Block with Uniform Transition. Espacenet, Sep. 25, 2025, Sep. 6, 2019, Year 2019 (Year: 2019).*
International Search Report issued Nov. 16, 2021 in PCT/JP2021/035176 (with English translation), 5 pages.
Written Opinion issued Nov. 16, 2021 in PCT/JP2021/035176 (with English translation), 8 pages.
Extended European Search Report issued Sep. 19, 2024, received on Oct. 1, 2024, in corresponding European Patent Application No. 21872581.0, 5 pages.

* cited by examiner

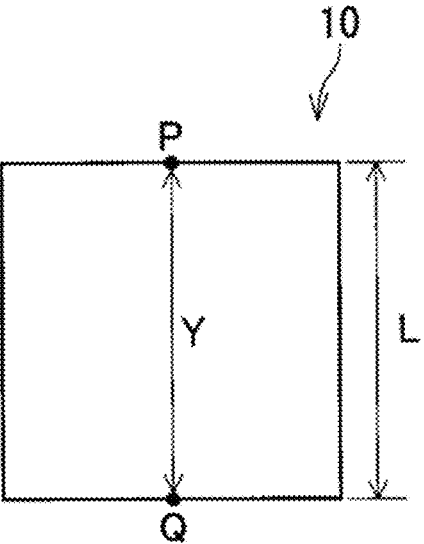

METHOD FOR PRODUCING ZIRCONIA SINTERED BODY

TECHNICAL FIELD

The present invention relates to a method for producing a zirconia sintered body.

BACKGROUND ART

For years, metal has been used for a range of dental products, including, for example, prostheses (such as veneer crowns, crowns, and post crowns), orthodontic products, and products for dental implants. However, metals lack aesthetic quality because of the colors that are distinctively different from the color of natural teeth, and can cause allergic reaction when released from these products. These issues involving the use of metal have been addressed by dental products that use ceramic materials such as aluminum oxide (alumina) and zirconium oxide (zirconia) as alternative materials of metal. Particularly, zirconia excels in strength, and has relatively good aesthetics, and this, combined with the declining price of zirconia, has created a high demand for this material.

In fabrication of a dental prosthesis with zirconia, a block unit or a disc-shaped work for milling (a material to be milled) that has been pre-sintered at a temperature about 400° C. to 700° C. below the temperature that produces an ideal sintered body is cut into a shape of a dental prosthesis with CAD/CAM equipment. The resulting workpiece of unsintered zirconia is then sintered by being held at a temperature as high as 1,400° C. to 1,650° C. The whole process from the start of temperature increase to the end of temperature decrease typically takes a total of 6 to 12 hours, including the retention period between temperature increase and temperature decrease. In response to a growing demand for short firing, a furnace is proposed that enables firing in a short time period, as described in Patent Literatures 1 and 2.

Recently, there is increasing use of a yttria multi-layered zirconia blank, which is a work for milling having a plurality of layers with different stabilizer (for example, yttria) contents (see, for example, Patent Literature 3), in order to achieve both strength and aesthetics in a dental prosthesis using zirconia.

CITATION LIST

Patent Literature

Patent Literature 1: JP 2015-531048 T
Patent Literature 2: JP 2019-524298 T
Patent Literature 3: WO2020/138316

SUMMARY OF INVENTION

Technical Problem

Patent Literatures 1 to 3 disclose furnaces for firing zirconia-containing ceramics in a short time period, along with schedule conditions. However, investigations by the present inventor revealed that, with conventional short firing schedules, stripes occur between layers having different yttria (stabilizer) contents, though the sintered body obtained can exhibit the shade and strength ideal as a dental prosthesis.

It is accordingly an object of the present invention to provide a method of production of a zirconia sintered body by which a zirconia molded body or zirconia pre-sintered body having a plurality of layers containing different amounts of stabilizer is sintered in a short time period to produce a zirconia sintered body having hardly noticeable stripes between layers differing in the amount of stabilizer. Another object of the present invention is to provide a method of production of a zirconia sintered body by which shade and strength as ideal as a dental prosthesis fired under normal conditions can be reproduced, despite that the method sinters a zirconia molded body or zirconia pre-sintered body in a short time period.

Solution to Problem

The present inventor conducted intensive studies to find a solution to the foregoing problem, and found that a zirconia sintered body having hardly noticeable stripes between layers differing in the amount of stabilizer can be obtained even by short firing when a specific short firing schedule is applied to a zirconia molded body or zirconia pre-sintered body having a plurality of layers containing different amounts of stabilizer. The present invention was completed after further studies based on this finding.

Specifically, the present invention includes the following.

[1] A method for producing a zirconia sintered body, comprising a firing step of firing a zirconia molded body or a zirconia pre-sintered body, the zirconia molded body or the zirconia pre-sintered body comprising a plurality of layers containing a stabilizer, the plurality of layers including layers having different stabilizer contents, the firing step comprising at least three stages of temperature-increasing process including a first temperature-increasing step (H1), a second temperature-increasing step (H2), and a third temperature-increasing step (H3), the method satisfying HR2=more than 0° C./min and less than 50° C./min, HR3=5° C./min or more and 150° C./min or less, and HR3/HR2>1, where HR2 is a rate of temperature increase in the second temperature-increasing step (H2), and HR3 is a rate of temperature increase in the third temperature-increasing step (H3), the temperature-increasing process having start temperatures that are 1,000° C. or less in H1, more than 1,250° C. and 1,450° C. or less in H2, and 1,450° C. or more and 1,550° C. or less in H3, the temperature-increasing process having end temperatures that are more than 1,250° C. and 1,450° C. or less in H1, 1,450° C. or more and 1,550° C. or less in H2, and 1,500° C. or more and 1,750° C. or less in H3.

[2] The method for producing a zirconia sintered body according to [1], wherein HR1 is 40 to 500° C./min, where HR1 is a rate of temperature increase in the first temperature-increasing step (H1).

[3] The method for producing a zirconia sintered body according to [1] or [2], wherein the stabilizer contents in the layers having different stabilizer contents differ by 0.1 mol % or more from one another.

[4] The method for producing a zirconia sintered body according to any one of [1] to [3], wherein the stabilizer is yttria.

[5] The method for producing a zirconia sintered body according to [4], wherein the content of the yttria relative to the total mole of the zirconia and the yttria is 2.5 mol % or more and 7.5 mol % or less in all of the layers in said plurality of layers.

[6] The method for producing a zirconia sintered body according to any one of [1] to [5], wherein HR2 is 2 to 30° C./min.

[7] The method for producing a zirconia sintered body according to any one of [1] to [6], wherein HR3 is 10 to 100° C./min.

[8] The method for producing a zirconia sintered body according to any one of [1] to [7], wherein HR3/HR2>1.5.

[9] The method for producing a zirconia sintered body according to any one of [1] to [8], wherein the temperature-increasing process has a highest firing temperature of 1,400 to 1,750° C., and a retention time at the highest firing temperature is 30 minutes or less.

[10] The method for producing a zirconia sintered body according to [9], which further comprises a temperature-decreasing step, and the temperature-decreasing step has a rate of temperature decrease of 10° C./min or more from the highest firing temperature of the temperature-increasing process to 800° C.

[11] The method for producing a zirconia sintered body according to any one of [1] to [10], wherein the firing step has a total firing time of 120 minutes or less from a start of temperature increase in the first temperature-increasing step (H1) to an end of a retention time at a highest firing temperature.

[12] The method for producing a zirconia sintered body according to any one of [1] to [11], wherein 55% or more of the zirconia molded body or the zirconia pre-sintered body are monoclinic in crystal system.

[13] The method for producing a zirconia sintered body according to any one of [1] to [12], wherein at least a part of the stabilizer is not dissolved in zirconia as a solid solution in the zirconia molded body or the zirconia pre-sintered body.

[14] The method for producing a zirconia sintered body according to any one of [1] to [13], wherein the zirconia molded body or the zirconia pre-sintered body has a predetermined shape of a dental product.

[15] The method for producing a zirconia sintered body according to [14], wherein the dental product is a dental prosthesis.

Advantageous Effects of Invention

According to a method of production of a zirconia sintered body of the present invention, a method of production of a zirconia sintered body can be provided by which a zirconia molded body or zirconia pre-sintered body having a plurality of layers containing different amounts of stabilizer is sintered in a short time period to produce a zirconia sintered body having hardly noticeable stripes between layers differing in the amount of stabilizer. The present invention can also provide a method of production of a zirconia sintered body by which shade and strength as ideal as a dental prosthesis fired under normal conditions (total hours of firing: 6 to 12 hours) can be reproduced despite short sintering.

BRIEF DESCRIPTION OF DRAWINGS

The FIG. is a schematic view of a zirconia pre-sintered body according to the present invention.

DESCRIPTION OF EMBODIMENTS

A zirconia sintered body that does not show stripes between layers containing different amounts of stabilizer can be obtained by sintering a zirconia molded body or zirconia pre-sintered body in a short time period (for example, a total firing time of 120 minutes or less) using a method of production of a zirconia sintered body of the present invention. Though the reason for this is unclear, the present inventor presumes that stripes in a zirconia sintered body obtained by short firing become more clearly visible as the difference of translucency (hereinafter, also referred to as $\Delta L(W-B)$) between adjacent layers containing different amounts of stabilizer increases, and less noticeable as the difference of $\Delta L(W-B)$ decreases.

In finding a countermeasure, the present inventor discovered the phenomenon that, in short firing, the temperature range in which changes occur in the rate of increase of $\Delta L(W-B)$ in response to temperature increase varies with the amount of the stabilizer contained in the layers. It follows from this that the overall difference of $\Delta L(W-B)$ between layers containing different amounts of stabilizer can be reduced when the differences of $\Delta L(W-B)$ between layers containing different amounts of stabilizer are held as small as possible in short firing by quickly firing a zirconia molded body or zirconia pre-sintered body with an increased rate of temperature increase in a temperature range in which $\Delta L(W-B)$ is more likely to be different, while the $\Delta L(W-B)$ of the zirconia molded body or zirconia pre-sintered body being heated is increased as a whole by slowing the rate of temperature increase in a specific temperature range in which the $\Delta L(W-B)$ of adjacent layers containing different amounts of stabilizer increases by about the same amount (that is, $\Delta L(W-B)$ is less likely to be different from layer to layer). This probably explains why the zirconia sintered body obtained shows hardly noticeable stripes, or no clearly visible boundaries between layers, despite short sintering.

The present invention is described below in detail.

The furnace used for firing in the present invention is an atmospheric furnace. The furnace may be a box furnace, a crucible furnace, a tube furnace, an elevator furnace, a continuous furnace, or a rotary kiln. It is also possible to use a resistance heating furnace, an induction heating furnace, a direct-current electric furnace, an IH furnace, a high-frequency furnace, or a microwave furnace. The heating element may be, for example, a metallic heating element, silicon carbide, molybdenum disilicate, lanthanum chromite, molybdenum, carbon, or tungsten. The susceptor may be SiC. The furnace may be a combination of two or more of these furnaces. Heat efficiency improves, and the heat in the furnace can be more easily maintained during firing when the furnace has a smaller volume in the chamber where a pedestal for placing a zirconia molded body or a zirconia pre-sintered body of a predetermined shape such as a crown is placed.

A zirconia molded body of the present invention is a molded body of zirconia that is unfired or unsintered. A zirconia molded body of the present invention may be partially-stabilized zirconia or fully stabilized zirconia. The term "unsintered" in the present invention refers to a state where reaction has not taken place in areas of contact between zirconia powder particles. A zirconia pre-sintered body of the present invention can be a precursor (intermediate product) of a zirconia sintered body. In the present invention, "zirconia pre-sintered body" means, for example, a block formed while zirconia particles (powder) are not fully sintered. In this specification, the upper limits and lower limits of numeric ranges (for example, rate of temperature increase, rate of temperature decrease, firing time, temperature, ratios of rates, and contents of components (for example, stabilizer)) can be combined appropriately.

A method of production of a zirconia sintered body of the present invention comprises at least three stages of temperature-increasing process. The temperature-increasing process includes a first temperature-increasing step H1, a second temperature-increasing step H2, and a third temperature-increasing step H3, with a different rate of temperature increase in each temperature-increasing step. The temperature-increasing process may include only these three temperature-increasing steps, or may include other temperature-increasing steps.

First Temperature-Increasing Step (H1)

In the first temperature-increasing step (H1) of a method of production of a zirconia sintered body of the present invention, a zirconia molded body or zirconia pre-sintered body is heated by instantaneously increasing temperature to the end temperature of the first temperature-increasing step (H1) in a furnace at room temperature or at a heated temperature of higher than room temperature and 1,000° C. or less. Preferably, the zirconia molded body or zirconia pre-sintered body before firing in the first temperature-increasing step (H1) is one having a predetermined shape of a dental product. Examples of the dental product include dental prostheses (such as veneer crowns, crowns, and post crowns), orthodontic products, and products for dental implants. The zirconia molded body or zirconia pre-sintered body to be heated may be one that has been processed with dental CAD/CAM equipment, or one fabricated by a denturist using a process such as milling.

For firing, a zirconia molded body or a zirconia pre-sintered body to be heated may be directly placed on a muffle member of a furnace, or may be placed in a furnace using a tray, a pedestal, or a pin made of ceramic or high-melting-point metal. Alternatively, ceramic beads may be used to place a zirconia molded body or a zirconia pre-sintered body.

The start temperature of the first temperature-increasing step (H1) is not particularly limited, as long as it is 1,000° C. or less. The preferred start temperature is room temperature to 1,000° C., more preferably room temperature to 450° C., even more preferably room temperature to 400° C., particularly preferably room temperature to 300° C. The end temperature of the first temperature-increasing step (H1) is 1,250 to 1,450° C. In view of further reduction of work time, the preferred end temperature is 1,300° C. or more. In view of reducing the transparency difference between layers having different yttria (stabilizer) contents, the end temperature of the first temperature-increasing step (H1) is more preferably 1,350° C. or more, even more preferably 1,400° C. or more.

When the rate of temperature increase in the first temperature-increasing step (H1) is HR1, it is preferable in view of further reduction of work time that HR1 be 40° C./min or more, more preferably 50° C./min or more, even more preferably 60° C./min or more, particularly preferably 70° C./min or more. HR1 is preferably 500° C./min or less, more preferably 450° C./min or less, even more preferably 400° C./min, particularly preferably 350° C./min or less. When HR1 is more than 500° C./min, fractures or cracks may occur during firing. When water used for work or a staining color liquid is present in the zirconia molded body or zirconia pre-sintered body subjected to the first temperature-increasing step (H1), the first temperature-increasing step (H1) may be started after drying for 1 to 20 minutes, preferably 5 to 15 minutes, at 300° C. or less. A certain preferred embodiment is, for example, a method of production of a zirconia sintered body in which HR1/HR3>1. More preferably, HR1/HR3>1.5. Even more preferably, HR1/HR3>2.

Second Temperature-Increasing Step (H2)

In a method of production of a zirconia sintered body of the present invention, HR2 is more than 0° C./min, where HR2 is the rate of temperature increase in the second temperature-increasing step (H2). In view of further reduction of work time, HR2 is preferably 1° C./min or more, more preferably 2° C./min or more, even more preferably 3° C./min or more, particularly preferably 4° C./min or more. HR2 is less than 50° C./min.

In view of providing a zirconia sintered body having even superior lightness and translucency, and reducing generation of stripes between layers having different yttria contents, HR2 is preferably less than 40° C./min, more preferably 35° C./min or less, even more preferably 30° C./min or less, particularly preferably 20° C./min or less.

The start temperature of the second temperature-increasing step (H2) is 1,250 to 1,450° C. In view of further reduction of work time, the start temperature of the second temperature-increasing step (H2) is preferably 1,300° C. or more. In view of reducing the transparency difference between layers having different yttria (stabilizer) contents, the start temperature of the second temperature-increasing step (H2) is more preferably 1,350° C. or more, even more preferably 1,400° C. or more. The end temperature of the second temperature-increasing step (H2) is 1,450 to 1,550° C. In view of further reduction of work time, the end temperature of the second temperature-increasing step (H2) is preferably 1,470° C. or more, more preferably 1,490° C. or more, even more preferably 1,500° C. or more. In view of providing a zirconia sintered body having even superior lightness, translucency, and saturation, and reducing generation of stripes between layers having different yttria contents while improving the color development of a composite oxide when the zirconia molded body or zirconia pre-sintered body contains a composite oxide, the end temperature of H2 is preferably 1,540° C. or less, more preferably 1,530° C. or less, even more preferably 1,520° C. or less.

Third Temperature-Increasing Step (H3)

When the rate of temperature increase in the third temperature-increasing step (H3) is HR3, HR3/HR2>1 in view of reducing the transparency difference between layers having different yttria (stabilizer) contents, and reducing generation of stripes between layers having different yttria contents when a zirconia molded body or zirconia pre-sintered body having layers containing different amounts of stabilizer is used for short firing. In view of providing a zirconia sintered body having even superior lightness, translucency, and saturation, and further reducing generation of stripes between layers having different yttria contents while improving the color development of a composite oxide when the zirconia molded body or zirconia pre-sintered body contains a composite oxide, it is preferable that HR3/HR2>1.2, more preferably HR3/HR2>1.5, even more preferably HR3/HR2>2. HR3 is 5° C./min or more. In view of further reduction of work time and reducing generation of stripes between layers having different yttria contents, HR3 is preferably 8° C./min or more, more preferably 9° C./min or more, even more preferably 10° C./min or more. HR3 is 150° C./min or less, preferably 100° C./min or less, more preferably 50° C./min or less in view of providing a zirconia sintered body having even superior saturation, and reducing generation of stripes while improving the color development of a composite oxide when the zirconia molded body or zirconia pre-sintered body contains a composite oxide.

The start temperature of the third temperature-increasing step (H3) is 1,450 to 1,550° C. In view of further reduction of work time and reducing generation of stripes between layers having different yttria contents, the start temperature of the third temperature-increasing step (H3) is preferably 1,470° C. or more, more preferably 1,490° C. or more, even more preferably 1,500° C. or more. The start temperature of H3 is preferably 1,540° C. or less, more preferably 1,530° C. or less, even more preferably 1,520° C. or less in view of providing a zirconia sintered body having even superior lightness, translucency, and saturation, and improving the color development of a composite oxide when the zirconia molded body or zirconia pre-sintered body contains a composite oxide.

The end temperature of the third temperature-increasing step (H3) is 1,500 to 1,750° C. In view of providing a zirconia sintered body having even superior lightness, translucency, and saturation, and improving the color development of a composite oxide when the zirconia molded body or zirconia pre-sintered body contains a composite oxide, the end temperature of the third temperature-increasing step (H3) is preferably 1,510° C. or more, more preferably 1,530° C. or more, even more preferably 1,550° C. or more. The end temperature of H3 is preferably 1,700° C. or less, more preferably 1,650° C. or less, even more preferably 1,600° C. or less in view of further reduction of work time, and providing a zirconia sintered body having even superior lightness, translucency, and saturation, and reducing generation of stripes between layers having different yttria contents while improving the color development of a composite oxide when the zirconia molded body or zirconia pre-sintered body contains a composite oxide.

The zirconia molded body or zirconia pre-sintered body used for a method of production of a zirconia sintered body of the present invention is preferably one that contains, in addition to zirconia, a stabilizer capable of reducing a phase transformation of zirconia. Such a zirconia molded body or zirconia pre-sintered body is preferably a zirconia molded body or zirconia pre-sintered body in which at least a part of the stabilizer is not dissolved in zirconia as a solid solution. The stabilizer is preferably one capable of forming partially stabilized zirconia.

A zirconia molded body or zirconia pre-sintered body used for a method of production of a zirconia sintered body of the present invention comprises a plurality of layers containing a stabilizer, and the plurality of layers includes layers having different stabilizer contents relative to the total mole of zirconia and stabilizer. The number of layers having different stabilizer contents is not particularly limited, as long as it is two or more. The number of layers having different stabilizer contents may be three, four, five, or six. The zirconia molded body or zirconia pre-sintered body may additionally comprise two or more layers having the same stabilizer content, provided that the zirconia molded body or zirconia pre-sintered body comprises layers having different stabilizer contents. With the zirconia molded body or zirconia pre-sintered body comprising layers having different stabilizer contents, it is possible to appropriately set the translucency and strength needed for different portions (layers) of the same material in a zirconia sintered body obtained by short firing. Preferably, the stabilizer contents in layers having different stabilizer contents differ by 0.1 mol % or more from one another. In view of achieving the translucency and strength suited for dental use, the difference of stabilizer content is more preferably 0.3 mol % or more, even more preferably 0.5 mol % or more. Preferably, the stabilizer contents in layers having different stabilizer contents differ by 3 mol % or less from one another. In view of achieving the translucency and strength suited for dental use, the difference of stabilizer content is more preferably 2.5 mol % or less, even more preferably 2 mol % or less.

In view of achieving the translucency and strength suited for dental use, it is preferable in a zirconia molded body or zirconia pre-sintered body used for a method of production of a zirconia sintered body of the present invention that the stabilizer (preferably yttria) content relative to the total mole of zirconia and stabilizer show an unchanging pattern of increase or decrease from one end to the other end of the zirconia pre-sintered body on a straight line extending along a first direction from one end to the other end of the zirconia pre-sintered body. In other words, it is preferable that the stabilizer (preferably yttria) content monotonously increase or decrease. This is described below with reference to the FIG. showing a schematic view of a zirconia pre-sintered body. It is preferable that the pattern of increase or decrease of stabilizer content do not change in the opposite direction on a straight line extending along a first direction Y from one end P to the other end Q of the zirconia pre-sintered body 10 of the FIG. Specifically, when the stabilizer content is in a pattern of decrease on a straight line from one end P to the other end Q, it is preferable that there exist no interval in which the stabilizer content essentially increases.

Examples of the stabilizer include oxides such as calcium oxide (CaO), magnesium oxide (MgO), yttria, cerium oxide (CeO$_2$), scandium oxide (Sc$_2$O$_3$), niobium oxide (Nb$_2$O$_5$), lanthanum oxide (La$_2$O$_3$), erbium oxide (Er$_2$O$_3$), praseodymium oxide (Pr$_6$O$_{11}$), samarium oxide (Sm$_2$O$_3$), europium oxide (Eu$_2$O$_3$), and thulium oxide (Tm$_2$O$_3$). The stabilizer may be used alone, or two or more thereof may be used in combination. The stabilizer content in a zirconia pre-sintered body and a sintered body thereof of the present invention can be measured, for example, by inductively coupled plasma (ICP) emission spectral analysis or x-ray fluorescence analysis. The stabilizer content in a zirconia pre-sintered body or a sintered body thereof of the present invention is preferably 0.1 to 18 mol %, more preferably 1 to 15 mol %, even more preferably 2 to 8 mol % relative to the total mole of zirconia and stabilizer. In view of the strength and translucency of the zirconia sintered body obtained, the zirconia molded body or zirconia pre-sintered body preferably contains yttria as a stabilizer. In all of the layers in the plurality of layers of the zirconia molded body or zirconia pre-sintered body, the yttria content is preferably 2.5 mol % or more, more preferably 3 mol % or more, even more preferably 3.5 mol % or more, particularly preferably 3.8 mol % or more relative to the total mole of zirconia and yttria. The zirconia sintered body can have improved translucency with a yttria content of 2.5 mol % or more. In all of the layers in the plurality of layers, the yttria content is preferably 7.5 mol % or less, more preferably 7.0 mol % or less, even more preferably 6.5 mol % or less, particularly preferably 6.0 mol % or less relative to the total mole of zirconia and yttria. A decrease in the strength of the zirconia sintered body obtained can be reduced with a yttria content of 7.5 mol % or less. A certain preferred embodiment (X-1) is, for example, a method of production of a zirconia sintered body that comprises a plurality of layers containing yttria as the stabilizer contained in the zirconia molded body or zirconia pre-sintered body, and in which the plurality of layers includes two or more layers having different yttria contents, with the layer ($Y_H$) with the highest yttria content having a yttria content of 3.5 mol % or more and 7.5 mol % or less, the layer ($Y_L$) with the lowest yttria content having a yttria content of 2.5 mol % or more and 7.0 mol % or less, and the ratio of the yttria content in layer ($Y_H$) to the yttria content in layer ($Y_L$)>1. In the preferred embodiment (X-1), it is more preferable that the yttria content in the layer ($Y_H$) with the highest yttria content be 3.8 mol % or more and 7.5 mol % or less, and that the yttria content in the layer ($Y_L$) with the lowest yttria content be 3.0 mol % or more and 6.5 mol % or less. It is even more preferable that the yttria content in the layer ($Y_H$) with the highest yttria content be 3.8 mol % or more and 7.0 mol % or less, and that the yttria content in the layer ($Y_L$) with the lowest yttria content be 3.0 mol % or more and 6.0 mol % or less.

In a zirconia molded body or zirconia pre-sintered body of the present invention, it is preferable that at least a part of the stabilizer be not dissolved in zirconia as a solid solution. Whether a part of stabilizer is not dissolved in zirconia as a solid solution can be determined from an XRD pattern, for example. The presence of peaks derived from the stabilizer in an XRD pattern of the zirconia pre-sintered body means the presence of a stabilizer that is not dissolved in zirconia as a solid solution in the zirconia molded body or zirconia pre-sintered body. A peak derived from the stabilizer is basically not observable in the XRD pattern when the stabilizer is fully dissolved as a solid solution. It is, however, possible, depending on the crystal state or other conditions of the stabilizer, that the stabilizer is not dissolved in zirconia as a solid solution even when the XRD pattern does not show peaks for stabilizers. When the predominant crystal system of zirconia is tetragonal and/or cubic and there is no peak attributed to the stabilizer in the XRD pattern, the stabilizer can be thought of having dissolved in zirconia as a solid solution for the most part, basically completely. In a zirconia molded body or zirconia pre-sintered body of the present invention, it is not required that the stabilizer be fully dissolved in zirconia as a solid solution. In the present invention, "stabilizer being dissolved as a solid solution" means that, for example, the elements (atoms) contained in the stabilizer are dissolved in zirconia as a solid solution.

In a zirconia molded body or zirconia pre-sintered body of the present invention, the percentage presence $f_y$ of yttria not dissolved in zirconia as a solid solution (hereinafter, also referred to as "undissolved yttria") can be calculated using the following mathematical expression (1). The percentage presence $f_y$ of undissolved yttria is preferably more than 0%, more preferably 1% or more, even more preferably 2% or more, particularly preferably 3% or more. The upper limit of percentage presence $f_y$ of undissolved yttria may be, for example, 15% or less. However, the upper limit of percentage presence $f_y$ of undissolved yttria preferably depends on the yttria content of the zirconia molded body or zirconia pre-sintered body. The percentage presence $f_y$ may be 7% or less when the yttria content is 2.5 mol % or more and less than 4.5 mol %. The percentage presence $f_y$ may be 11% or less when the yttria content is 4.5 mol % or more and less than 5.8 mol %. The percentage presence $f_y$ may be 15% or less when the yttria content is 5.8 mol % or more and less than 7.5 mol %.

In a zirconia molded body or zirconia pre-sintered body of the present invention, $f_y$ is preferably 0.5% or more, more preferably 1.0% or more, even more preferably 2.0% or more when the yttria content is 2.5 mol % or more and less than 4.5 mol %. The percentage presence $f_y$ of undissolved yttria is preferably 1% or more, more preferably 2% or more, even more preferably 3% or more when the yttria content is 4.5 mol % or more and less than 5.8 mol %. The percentage presence $f_y$ is preferably 2% or more, more preferably 3% or more, even more preferably 4% or more when the yttria content is 5.8 mol % or more and 7.5 mol % or less. In a zirconia pre-sintered body of the present invention, $f_m/f_y$ is preferably 20 to 200, more preferably 25 to 100, even more preferably 30 to 60 when the yttria content is 2.5 mol % or more and less than 4.5 mol %. The ratio $f_m/f_y$ is preferably 5 to 45, more preferably 10 to 40, even more preferably 15 to 35 when the yttria content is 4.5 mol % or more and less than 5.8 mol %. The ratio $f_m/f_y$ is preferably 2 to 40, more preferably 5 to 35, even more preferably 10 to 30 when the yttria content is 5.8 mol % or more and 7.5 mol % or less.

[Math. 1]

$$f_y(\%) = \frac{I_y(111)}{I_y(111) + I_m(111) + I_m(11-1) + I_t(111) + I_c(111)} \times 100 \tag{1}$$

In mathematical expression (1), $I_y(111)$ represents the peak intensity of the (111) plane of yttria near $2\theta=29°$ in an XRD pattern by CuKα radiation, $I_m(111)$ and $I_m(11-1)$ represent the peak intensities of the (111) plane and (11-1) plane, respectively, of the monoclinic crystal system of zirconia, $I_t(111)$ represents the peak intensity of the (111) plane of the tetragonal crystal system of zirconia, and $I_c(111)$ represents the peak intensity of the (111) plane of the cubic crystal system of zirconia.

By substituting $I_y(111)$ for other peaks, the mathematical expression (1) can be used to calculate the percentage presence of an undissolved fraction of a stabilizer other than yttria.

It is preferable that the zirconia in a zirconia molded body or zirconia pre-sintered body of the present invention be predominantly monoclinic in crystal system. In the present invention, "being predominantly monoclinic in crystal system" means that the fraction $f_m$ of the monoclinic crystal system of zirconia calculated from the mathematical expression (2) below is 50% or more relative to the total amount of all the crystal systems (monoclinic, tetragonal, and cubic) of the zirconia. In a zirconia molded body or zirconia pre-sintered body of the present invention, the fraction $f_m$ of the monoclinic crystal system in zirconia calculated from the mathematical expression (2) below is preferably 55% or more, more preferably 60% or more, even more preferably 70% or more, yet more preferably 75% or more, particularly preferably 80% or more, still more preferably 85% or more, most preferably 90% or more relative to the total amount of the monoclinic, tetragonal, and cubic crystal systems. The fraction $f_m$ of monoclinic crystal system can be calculated from the mathematical expression (2) below, using peaks in an X-ray diffraction (XRD) pattern by CuKα radiation. The predominant crystal system of the zirconia molded body or zirconia pre-sintered body possibly contributes to elevating the shrinkage temperature and reducing the firing time.

In a zirconia molded body or zirconia pre-sintered body of the present invention, the peaks for tetragonal and cubic crystal systems may be essentially undetectable. That is, the fraction $f_m$ of the monoclinic crystal system may be 100%.

[Math. 2]

$$f_m(\%) = \frac{I_m(111) + I_m(11-1)}{I_m(111) + I_m(11-1) + I_t(111) + I_c(111)} \times 100 \qquad (2)$$

In mathematical expression (2), $I_m(111)$ and $I_m(11\text{-}1)$ represent the peak intensities of the (111) plane and (11-1) plane, respectively, of the monoclinic crystal system of zirconia, $I_t(111)$ represents the peak intensity of the (111) plane of the tetragonal crystal system of zirconia, and $I_c(111)$ represents the peak intensity of the (111) plane of the cubic crystal system of zirconia.

The zirconia molded body or zirconia pre-sintered body may optionally comprise an additive. Examples of the additive include binders, colorants (including pigments, complex pigments, and fluorescent agents), alumina ($Al_2O_3$), titanium oxide ($TiO_2$), and silica ($SiO_2$). The additive may be used alone, or two or more thereof may be used as a mixture.

Examples of the binders include polyvinyl alcohol, methyl cellulose, carboxymethyl cellulose, acrylic binders, wax binders (e.g., paraffin wax), polyvinyl butyral, polymethyl methacrylate, ethyl cellulose, polyethylene, polypropylene, an ethylene-vinyl acetate copolymer, polystyrene, atactic polypropylene, methacrylic resin, and stearic acid.

Examples of the pigments include oxides of at least one element selected from the group consisting of Ti, V, Cr, Mn, Fe, Co, Ni, Zn, Y, Zr, Sn, Sb, Bi, Ce, Pr, Sm, Eu, Gd, Tb, and Er (specifically, for example, NiO, $Cr_2O_3$), preferably oxides of at least one element selected from the group consisting of Ti, V, Cr, Mn, Fe, Co, Ni, Zn, Y, Zr, Sn, Sb, Bi, Ce, Pr, Sm, Eu, Gd, and Tb, more preferably oxides of at least one element selected from the group consisting of Ti, V, Cr, Mn, Fe, Co, Ni, Zn, Y, Zr, Sn, Sb, Bi, Ce, Sm, Eu, Gd, and Tb. A zirconia molded body or a zirconia pre-sintered body of the present invention may be a zirconia molded body or a zirconia pre-sintered body that does not contain erbium oxide ($Er_2O_3$). Examples of the complex pigments include composite oxides, for example, such as $(Zr,V)O_2$, $Fe(Fe,Cr)_2O_4$, $(Ni,Co,Fe)(Fe,Cr)_2O_4ZrSiO_4$, and $(Co,Zn)Al_2O_4$. Examples of the fluorescent agents include $Y_2SiO_5$:Ce, $Y_2SiO_5$:Tb, (Y,Gd,Eu)BO_3, $Y_2O_3$:Eu, YAG:Ce, $ZnGa_2O_4$:Zn, and $BaMgAl_{10}O_{17}$:Eu.

The method used to produce a zirconia molded body in the present invention is not particularly limited. An example is a method that includes a step of pressing a mixed powder of zirconia (preferably, a zirconia powder that is predominantly monoclinic in crystal system) and the stabilizer into a zirconia molded body under a pressure of 175 MPa or higher. By being pressed under this pressure, the mixed powder can form a zirconia molded body (and, in turn, a zirconia sintered body) having an increased bulk density, irrespective of the thickness. As used herein, "pressure of 175 MPa or higher" means the maximum pressure of press forming.

The method used to produce a zirconia pre-sintered body in the present invention is not particularly limited. In an example method, a zirconia molded body formed from a raw material powder containing zirconia particles (preferably, zirconia particles that are predominantly monoclinic in crystal system) and a stabilizer is fired (pre-sintered) at a temperature that does not sinter the zirconia particles. The method of production of the zirconia molded body is as described above. An example of a method of producing a zirconia pre-sintered body of the present invention is described below. First, a raw material powder of zirconia molded body is produced. A powder of monoclinic zirconia and a powder of stabilizer (for example, a yttria powder) are used to prepare a mixture having a desired stabilizer (for example, yttria) content. The mixture is added into water to make a slurry, and the slurry is pulverized and mixed wet with a ball mill until the particles reach the desired particle size. After pulverization, the slurry is dried to granulate, using a spray dryer. The resultant powder is then fired to make a powder (primary powder) at a temperature (for example, 800 to 1,200° C.) that does not sinter the zirconia particles. A pigment may be added to the primary powder. The primary powder is then added into water to make a slurry, and the slurry is pulverized and mixed wet with a ball mill until the particles reach the desired particle size. After optionally adding an additive, such as a binder, to the pulverized slurry, the slurry is dried with a spray dryer to obtain a mixed powder (secondary powder). The secondary powder is filled into a predetermined die, and, after leveling the top surface and installing an upper die, pressure is applied with a uniaxial pressing machine to form the secondary powder into a zirconia molded body. The pressure applied for press forming of the mixed powder is preferably 175 MPa or higher. The zirconia molded body obtained may or may not be subjected to cold isostatic pressing (CIP).

The zirconia molded body or zirconia pre-sintered body may have a multilayer structure. When producing a multilayer zirconia pre-sintered body, the primary powder used in the method of production of a zirconia molded body may be divided into at least two (preferably four) separate portions to provide a multilayer structure in the zirconia molded body.

The zirconia pre-sintered body has a density of preferably 2.7 g/cm³ or more. The zirconia pre-sintered body has a density of preferably 4.0 g/cm³ or less, more preferably 3.8 g/cm³ or less, even more preferably 3.6 g/cm³ or less. Easy molding is possible with the density confined in these ranges. For example, the density can be calculated as a ratio of the mass of the pre-sintered body to the volume of the pre-sintered body.

The zirconia pre-sintered body has a three-point flexural strength of preferably 15 to 70 MPa, more preferably 18 to 60 MPa, even more preferably 20 to 50 MPa, particularly preferably 20 to 40 MPa. The flexural strength can be measured in compliance with ISO 6872:2015. For measurement, a specimen measuring 5 mm×10 mm×50 mm is used under the same conditions except for size. For surface finishing, the specimen surfaces, including the chamfered surface, are finished longitudinally with #600 sandpaper. The specimen is disposed in such an orientation that its widest face is perpendicular to the vertical direction (loading direction). In the flexure test, measurements are made at a span of 30 mm with a crosshead speed of 0.5 mm/min.

The zirconia molded body obtained in this fashion is pre-sintered to obtain a zirconia pre-sintered body. The pre-sintering temperature is, for example, preferably 800° C. or more, more preferably 900° C. or more, even more preferably 950° C. or more. For increased dimensional accuracy, the pre-sintering temperature is, for example, preferably 1,200° C. or less, more preferably 1,150° C. or less, even more preferably 1,100° C. or less. Conceivably, dissolution of the stabilizer does not proceed in these temperature ranges.

In a method of production of a zirconia sintered body of the present invention, the rate of temperature increase in each temperature-increasing step may be constant, or temperature may be increased stepwise by varying the rate of temperature increase while increasing temperature, provided that the temperature-increasing steps satisfy the start temperature, the end temperature, the range of temperature increasing rate, and the relationship HR3/HR2>1 noted above. For example, in certain embodiments, the temperature in the second temperature-increasing step may be increased at 50° C./min for 30 seconds after the start of temperature increase from the start temperature, and at 10° C./min after 30 seconds of temperature increase at 50° C./min. In other embodiments, the temperature in the third temperature-increasing step may be increased at 50° C./min for 30 seconds after the start of temperature increase from the start temperature, and at 10° C./min after 30 seconds of temperature increase at 50° C./min.

Retention Step

In a method of production of a zirconia sintered body of the present invention, it is preferable that the retention time at the highest end temperature (highest firing temperature) be 30 minutes or less. In view of further reduction of work time, the retention time is more preferably 10 to 25 minutes, even more preferably 15 to 20 minutes. The highest firing temperature is preferably 1,400 to 1,750° C. In view of providing a zirconia sintered body having superior lightness, translucency, and saturation, and enabling a composite oxide to better develop color when the zirconia molded body or zirconia pre-sintered body contains a composite oxide, the highest firing temperature is preferably 1,510° C. or more, more preferably 1,530° C. or more, even more preferably 1,550° C. or more. In view of further reduction of work time and providing a zirconia sintered body having even superior lightness, translucency, and saturation, and enabling a composite oxide to better develop color when the zirconia molded body or zirconia pre-sintered body contains a composite oxide, and reducing generation of stripes between layers having different yttria contents, the highest firing temperature is preferably 1,750° C. or less, more preferably 1,650° C. or less, even more preferably 1,600° C. or less. Preferably, the retention step immediately follows the third temperature-increasing step. However, another temperature-increasing step may be present between the third temperature-increasing step and the retention step, provided that the present invention can exhibit its effects. In embodiments that do not include a temperature-increasing step other than H1 to H3, the highest firing temperature is the end temperature of H3.

In view of further reduction of work time, the firing step has a total firing time of preferably 120 minutes or less, more preferably 90 minutes or less, even more preferably 75 minutes or less from the start of temperature increase in the first temperature-increasing step to the end of the retention time at the highest firing temperature.

Cooling Step (Temperature-Decreasing Step)

Preferably, a method of production of a zirconia sintered body of the present invention comprises a cooling step following the retention at the highest firing temperature for a predetermined time period. In the cooling step, the rate of temperature decrease from the highest firing temperature of the temperature-increasing process to 800° C. is preferably 10° C./min or more, more preferably 30° C./min or more, even more preferably 50° C./min or more. The method of temperature decrease may be any of cooling with outside intake air, water cooling, air cooling, gradual cooling, and standing to cool, or a combination of these. The end temperature of the cooling step depends on factors such as the type and capabilities of the furnace, and may be 950° C., 750° C., or 1,000° C.

A zirconia sintered body obtained by a method of production of the present invention has a color difference ΔE*ab of preferably 2.7 or less, more preferably 2.0 or less, even more preferably 1.6 or less, particularly preferably 0.8 or less because such a zirconia sintered body is suited as a dental product. Preferably, the color difference ΔE*ab is measured against the chromaticity of a zirconia sintered body of when it is fired in a normal fashion (total hours of firing: 6 to 12 hours). Chromaticity can be evaluated using the method described in the EXAMPLES section below. In the present specification, "total hours of firing" (or "total firing time") means a time period from the start of temperature increase in the first temperature-increasing step to the end of the retention time at the highest firing temperature in the firing step.

The difference between the lightness index L* of a zirconia sintered body obtained by a method of production of the present invention and the lightness index L* of a zirconia sintered body fired in a normal fashion (total hours of firing: 6 to 12 hours) is preferably 2.0 or less, more preferably 1.5 or less, even more preferably 1.0 or less because a zirconia sintered body with such a L* difference is suited as a dental product. The L*, a*, and b* of a zirconia sintered body obtained by a method of production of the present invention can be selected and set according to where the zirconia sintered body is intended for, for example, such as the cervical region, the body, or the incisal edge.

The present invention encompasses embodiments combining the foregoing features, provided that the present invention can exhibit its effects with such combinations made in various forms within the technical idea of the present invention.

EXAMPLES

The following describes the present invention in greater detail by way of Examples. It should be noted, however, that the present invention is in no way limited by the following Examples, and various changes may be made by a person with ordinary skill in the art within the technical idea of the present invention.

Example 1

Preparation of Raw Material Powder Used for Fabrication of Zirconia Pre-Sintered Body The raw material powder used to fabricate the zirconia pre-sintered body used in Example 1 was prepared as follows. First, a powder of monoclinic zirconia and a yttria powder were used to prepare a mixture in the compositions shown in Table 1, except for the color components. The mixture was added to water to prepare a slurry, and the slurry was mixed and pulverized to an average particle diameter of 0.13 μm or less by wet pulverization with a ball mill. After pulverization, the slurry was dried with a spray dryer, and the resulting powder was fired at a pre-sintering temperature of 950° C. for 2 hours to prepare a powder (primary powder). The average particle diameter can be determined by a laser diffraction scattering method. As a specific example of a laser diffraction scattering method, a 0.2% aqueous solution of sodium hexametaphosphate may be used as a dispersion medium for the measurement of average particle diameter by volume, using a laser diffraction particle size distribution analyzer (SALD-2300, manufactured by Shimadzu Corporation). The yttria contents in Table 1 are the contents of yttria relative to the total mole of zirconia and yttria.

Color components were added to the primary powder in the compositions shown in Table 1. After adding the color components, the powder was added to water to prepare a slurry, and the slurry was mixed and pulverized to an average particle diameter of 0.13 µm or less by wet pulverization with a ball mill. After adding a binder to the pulverized slurry, the slurry was dried with a spray dryer to prepare a powder (secondary powder). The secondary powder was used as a raw material powder for the production of a zirconia pre-sintered body, as described below.

Fabrication of Block of Zirconia Pre-Sintered Body

A block of zirconia pre-sintered body used for fabrication of a crown-shaped zirconia sintered body was produced by the method described below. First, the raw material powder was filled into a die having inside dimensions of 20 mm×25 mm, 15 g each for the first and second layers, in this order, as shown in Table 1. For primary pressing, the raw material powders were then pressed at a surface pressure of 300 kg/cm² for 90 seconds with a uniaxial pressing machine. The molded body (zirconia molded body) after primary pressing was subjected to CIP molding at 1,700 kg/cm² for 5 minutes to prepare a molded body having a layered structure. The molded body was fired at 1,000° C. for 2 hours to prepare a block of zirconia pre-sintered body.

The block of zirconia pre-sintered body was machined into different shapes for the evaluations of various properties described below, and was fired with the firing schedules shown in Table 2. The results of property evaluations will be described later. For the evaluation of $\Delta L(W-B)$ of zirconia sintered body, a zirconia sintered body was individually prepared for each layer, as described below.

Examples 2 to 5, and Comparative Example 1 and Reference Example 1

A secondary powder was prepared, and a block of zirconia pre-sintered body was fabricated in the same manner as in Example 1. A zirconia sintered body was prepared in the same manner as in Example 1, except that the firing schedule was changed as shown in Tables 2 and 3. The properties were evaluated as in Example 1.

Evaluation of $\Delta L(W-B)$ of Each Layer of Zirconia Sintered Body

In Examples 1 to 5, and Comparative Example 1 and Reference Example 1, a zirconia sintered body was individually prepared for layer 1 and layer 2 as shown in Table 1, using the method below. The zirconia sintered body was then measured for (L*,a*,b*) according to L*a*b* color system (JIS Z 8781-4:2013 Color Measurements—Part 4: CIE 1976 L*a*b* color space). $\Delta L(W-B)$ was calculated from each (L*,a*,b*) of the zirconia sintered body. The following formula (1) is used to determine $\Delta L(W-B)$, using the L value ($L_1$*) of the zirconia sintered body of when it is measured over a white background, and the L value ($L_2$*) of the zirconia sintered body of when it is measured over a black background.

$$\Delta L(W-B) = (L_1^*) - (L_2^*) \qquad (1)$$

First, a molded body was prepared with the raw material powder of each layer by pressing the raw material powder in a size that had been pre-adjusted to obtain a zirconia sintered body 1.2 mm thick. The molded body was then fired at 1,000° C. for 2 hours to prepare a zirconia pre-sintered body. The zirconia pre-sintered body was fired with the firing schedules shown in Tables 2 and 3 to prepare a zirconia sintered body, using the InFire HTC speed furnace (manufactured by Dentsply Sirona). The zirconia sintered body was polished with #600 abrasive paper on both surfaces to obtain a zirconia sintered body having a thickness of 1.2 mm. The zirconia sintered body of each layer was then measured over a white background and a black background with a dental colorimeter (7-band LED light source, Crystaleye; manufactured by Olympus Corporation) (n=3). The result of evaluation are presented in Tables 2 and 3 as mean values for n=3.

Aesthetic Evaluation of Crown-Shaped Zirconia Sintered Body

The zirconia sintered bodies of Examples 1 to 5, Comparative Example 1, and Reference Example 1 were visually evaluated for aesthetic quality in comparison to the appearance of natural teeth, using the method below. A commercially available shade guide providing shades similar to the shades of natural teeth can be used for evaluation. A specific example of such a commercially available shade guide is the VITA Classical shade guide manufactured by VITA under this trade name. First, the block of zirconia pre-sintered body was machined into a crown shape for front teeth, using the DWX-52DC milling machine (manufactured by Roland DG). After machining, the zirconia pre-sintered body was fired to obtain a zirconia sintered body of each Example and Comparative Example, following the firing schedules of Tables 2 and 3 using the InFire HTC speed furnace (manufactured by Dentsply Sirona).

The zirconia sintered body was visually evaluated by four testers, using the following criteria. The zirconia sintered body was determined as satisfying any of the following criteria when at least three out of the four testers made the same judgment. The results are presented in Tables 2 and 3.

Evaluation Criteria

Good: No stripes were observed between layers having different yttria contents, posing no problem for dental clinical practice Moderate: Stripes were slightly present between layers having different yttria contents, but the extent of stripes was acceptable for dental clinical practice Poor: Stripes were noticeable between layers having different yttria contents, and the result was unacceptable for clinical practice.

Strength Evaluation of Zirconia Sintered Body

The zirconia sintered bodies of Examples 1 to 5, Comparative Example 1, and Reference Example 1 were evaluated to confirm strength, using the method below. First, the block of zirconia pre-sintered body was machined to prepare ten cuboidal samples (1.7 mm×5.2 mm×20.2 mm), using the DWX-52DC milling machine (manufactured by Roland DG). After machining, the zirconia pre-sintered body was fired under the firing schedule conditions shown in Tables 2 and 3, using the InFire HTC speed furnace (manufactured by Dentsply Sirona). The zirconia sintered body after firing was polished with #1000 abrasive paper using a rotary grinding disc to prepare a cuboidal sample of sintered body measuring 1.2 mm×4 mm×14 mm in size. The sintered body sample was measured for three-point flexural strength in compliance with ISO 6872:2015, with the crosshead speed set to 0.5 mm/min, and the distance between supports (span) set at 12 mm (n=10). Tables 2 and 3 show the evaluation results as mean values for n=10.

Evaluation of $\Delta E^*ab$ of Crown-Shaped Zirconia Sintered Body

The zirconia sintered bodies of Examples 1 to 5 and Comparative Example 1 were compared with the zirconia sintered body of Reference Example 1 fired with a normal firing schedule, and the color difference $\Delta E^*ab$ (hereinafter, also referred to as "ΔE*") was calculated to confirm the shade difference, using the method below. First, the block of zirconia pre-sintered body was machined into a crown shape for front teeth, using the DWX-52DC milling machine (manufactured by Roland DG). After machining, the zirconia pre-sintered body was fired with the firing schedules of Tables 2 and 3 to prepare samples of the same shape, using the InFire HTC speed furnace. The fired sintered body samples were then measured for color with a dental colorimeter (7-band LED light source, Crystaleye; manufactured by Olympus Corporation), and the lightness, saturation, and color difference ΔE*ab were evaluated for the cervical, body, and incisal portions according to L*a*b* color system (JIS Z 8781-4:2013 Color Measurements—Part 4: CIE 1976 L*a*b* color space) (n=5). Table 4 shows the evaluation results as mean values for n=5. The color difference ΔE*ab is determined from the following formula (2) for two of the sintered body samples obtained with the firing schedules shown in Tables 2 and 3, using the lightness index L* and color coordinates a* and b* of the CIE 1976 L*a*b* color space.

$$\Delta E^* = \left\{ (L_1^* - L_2^*)^2 + (a_1^* - a_2^*)^2 + (b_1^* - b_2^*)^2 \right\}^{1/2} \quad (2)$$

Evaluation of Property Values

In Examples 1, 3 to 5 and Reference Example 1, the difference of ΔL(W−B) values in the layers of the zirconia sintered body was 0.79 to 1.03, and there were no noticeable stripes between the layers having different yttria contents in the aesthetic evaluation of the crown-shaped zirconia sintered body, confirming that the zirconia sintered body does not pose a problem for dental clinical practice. In the strength evaluation of the zirconia sintered body, the sintered body samples showed values of three-point flexural strength comparable to that of when the sintered body was fired with a normal firing schedule (Reference Example 1), and the three-point flexural strength did not pose a problem for dental use. In the evaluation of ΔE*ab of the crown-shaped zirconia sintered body, the zirconia sintered body had a color difference ΔE*ab of 2.7 or less compared to the sample fired with a normal firing schedule.

In Example 2, the difference of ΔL(W−B) values in the layers of the zirconia sintered body was 1.45, falling in the range acceptable for dental clinical practice, though slight stripes were observed between the layers having different yttria contents in the aesthetic evaluation of the crown-shaped zirconia sintered body. In the strength evaluation of the zirconia sintered body, the sintered body samples showed values of three-point flexural strength comparable to that of when the sintered body was fired with a normal firing schedule, and the three-point flexural strength did not pose a problem for dental use. In the evaluation of ΔE*ab of the crown-shaped zirconia sintered body, the zirconia sintered body had a color difference ΔE*ab of 2.7 or less compared to the sample fired with a normal firing schedule.

In Comparative Example 1, the three-point flexural strength and ΔE* did not pose a problem for dental use. However, the difference of ΔL(W−B) values in the layers of the zirconia sintered body was 2.7, and noticeable stripes were observed between the layers having different yttria contents in the aesthetic evaluation of the crown-shaped zirconia sintered body, making the zirconia sintered body unacceptable for clinical practice. A large difference of ΔL(W−B) values as in Comparative Example 1 is probably due to the firing schedule with a constant rate of temperature increase in the temperature range that influences translucency and shade. Patent Literature 2 (JP 2019-524298 T) will likely produce a result similar to that observed in Comparative Example 1 because of the firing schedule in which the firing profile above 1,000° C. involves one stage of temperature increase, or a constant rate of temperature increase, as shown in FIG. 3 of this patent literature.

TABLE 1

| Layers | Yttria content | Color components | | Fraction $f_m$ of monoclinic crystal system | Percentage presence $f_y$ of undissolved yttria |
| | | NiO | (Zr, V)O$_2$ | | |
|---|---|---|---|---|---|
| Layer 1 | 5 mol % | 0.012 | 0.019 | 85% | 3.0% |
| Layer 2 | 4 mol % | 0.015 | 0.025 | 91% | 2.0% |

TABLE 2

| | Example 1 | | | | Example 2 | |
| Steps | Rate of temperature increase (° C./min) | Start temperature (° C.) | End temperature (° C.) | Retention time (min) | Rate of temperature increase (° C./min) | Start temperature (° C.) |
|---|---|---|---|---|---|---|
| H1 | 50 | R.T. | 1400 | 0 | 150 | R.T. |
| H2 | 4 | 1400 | 1500 | 0 | 35 | 1400 |
| H3 | 10 | 1500 | 1560 | 16 | 150 | 1500 |
| Cooling step | −50 | 1560 | 800 | 0 | −50 | 1560 |
| Total firing time (min) | | 75 | | | | 29 |
| Results | ΔL(W − B) | | Difference of ΔL(W − B) of Layer 1 and Layer 2 (Absolute value) | | ΔL(W − B) | Difference of ΔL(W − B) of Layer 1 and Layer 2 (Absolute value) |
| Layer 1 | 15.71 | | 1.01 | | 15.08 | 1.45 |
| Layer 2 | 14.7 | | | | 13.63 | |
| Visual evaluation of aesthetics | | Good | | | | Moderate |
| Three-point flexural strength (MPa) | | 1098 | | | | 1083 |

TABLE 2-continued

| | Example 2 | | Example 3 | | | |
| | | | Rate of | | | |
| Steps | End temperature (° C.) | Retention time (min) | temperature increase (° C./min) | Start temperature (° C.) | End temperature (° C.) | Retention time (min) |
|---|---|---|---|---|---|---|
| H1 | 1400 | 0 | 50 | R.T. | 1400 | 0 |
| H2 | 1500 | 0 | 2 | 1400 | 1500 | 0 |
| H3 | 1560 | 16 | 10 | 1500 | 1560 | 16 |
| Cooling step | 800 | 0 | −50 | 1560 | 800 | 0 |
| Total firing time (min) | 29 | | | 100 | | |
| Results | Difference of ΔL(W − B) of Layer 1 and Layer 2 (Absolute value) | | ΔL(W − B) | | Difference of ΔL(W − B) of Layer 1 and Layer 2 (Absolute value) | |
| Layer 1 | 1.45 | | 15.89 | | 0.79 | |
| Layer 2 | | | 15.10 | | | |
| Visual evaluation of aesthetics | Moderate | | | | Good | |
| Three-point flexural strength (MPa) | 1083 | | | | 1026 | |

| | Example 4 | | | | Example 5 | | | |
| | Rate of temperature increase (° C./min) | Start temperature (° C.) | End temperature (° C.) | Retention time (min) | Rate of temperature increase (° C./min) | Start temperature (° C.) | End temperature (° C.) | Retention time (min) |
| Steps | | | | | | | | |
|---|---|---|---|---|---|---|---|---|
| H1 | 50 | R.T. | 1450 | 0 | 50 | R.T. | 1250 | 0 |
| H2 | 4 | 1450 | 1550 | 0 | 4 | 1250 | 1450 | 0 |
| H3 | 10 | 1550 | 1650 | 16 | 10 | 1450 | 1550 | 16 |
| Cooling step | −50 | 1560 | 800 | 0 | −50 | 1560 | 800 | 0 |
| Total firing time (min) | 80 | | | | 101 | | | |
| Results | ΔL(W − B) | | Difference of ΔL(W − B) of Layer 1 and Layer 2 (Absolute value) | | ΔL(W −B) | | Difference of ΔL(W − B) of Layer 1 and Layer 2 (Absolute value) | |
| Layer 1 | 16.08 | | 1.03 | | 16.06 | | 0.81 | |
| Layer 2 | 15.05 | | | | 15.25 | | | |
| Visual evaluation of aesthetics | Good | | | | Good | | | |
| Three-point flexural strength (MPa) | 1048 | | | | 1018 | | | |

TABLE 3

| | Comparative Example 1 | | | | Reference Example 1 | | | |
| | Rate of temperature increase (° C./min) | Start temperature (° C.) | End temperature (° C.) | Retention time (min) | Rate of temperature increase (° C./min) | Start temperature (° C.) | End temperature (° C.) | Retention time (min) |
| Steps | | | | | | | | |
|---|---|---|---|---|---|---|---|---|
| H1 | 35 | R.T. | 1560 | 30 | 10 | R.T. | 1550 | 120 |
| H2 | — | — | — | — | — | — | — | — |
| H3 | — | — | — | — | — | — | — | — |
| Cooling step | −45 | 1560 | 800 | 0 | −10 | 1550 | 100 | 0 |
| Total firing time (min) | 75 | | | | 275 | | | |

TABLE 3-continued

| | Comparative Example 1 | | | | Reference Example 1 | | | |
|---|---|---|---|---|---|---|---|---|
| Steps | Rate of temperature increase (° C./min) | Start temperature (° C.) | End temperature (° C.) | Retention time (min) | Rate of temperature increase (° C./min) | Start temperature (° C.) | End temperature (° C.) | Retention time (min) |
| Results | ΔL(W − B) | | Difference of ΔL(W − B) of Layer 1 and Layer 2 (Absolute value) | | ΔL(W − B) | | Difference of ΔL(W − B) of Layer 1 and Layer 2 (Absolute value) | |
| Layer 1 | 16.06 | | 2.7 | | 16.07 | | 0.8 | |
| Layer 2 | 13.36 | | | | 15.27 | | | |
| Visual evaluation of aesthetics | | | Poor | | | | Good | |
| Three-point flexural strength (MPa) | | | 1011 | | | | 1010 | |

TABLE 4

| Firing conditions | Measured portions | L | a | b | ΔE*ab |
|---|---|---|---|---|---|
| Example 1 | Cervical | 70.78 | 0.32 | 22.81 | 0.1 |
| | Body | 71.79 | −0.32 | 19.51 | 0.4 |
| | Incisal | 69.32 | −1.18 | 15.11 | 1.5 |
| Example 2 | Cervical | 70.52 | 0.46 | 22.39 | 0.4 |
| | Body | 71.29 | −0.25 | 19.02 | 0.6 |
| | Incisal | 69.01 | −0.68 | 15.03 | 1.9 |
| Example 3 | Cervical | 70.68 | 0.4 | 22.88 | 0.2 |
| | Body | 71.89 | −0.39 | 19.64 | 0.5 |
| | Incisal | 69.94 | −1.29 | 15.44 | 0.8 |
| Example 4 | Cervical | 70.46 | 0.59 | 22.29 | 0.6 |
| | Body | 70.98 | −0.31 | 18.98 | 0.9 |
| | Incisal | 69.87 | −0.72 | 14.91 | 1.3 |
| Example 5 | Cervical | 70.72 | 0.29 | 22.54 | 0.2 |
| | Body | 71.69 | −0.44 | 19.08 | 0.2 |
| | Incisal | 70.26 | −1.09 | 15.44 | 0.6 |
| Comparative Example 1 | Cervical | 71.24 | 0.39 | 21.03 | 1.7 |
| | Body | 73.01 | −0.2 | 18.24 | 1.5 |
| | Incisal | 71.58 | −0.7 | 14.69 | 1.4 |
| Reference Example 1 | Cervical | 70.76 | 0.3 | 22.69 | |
| | Body | 71.85 | −0.44 | 19.13 | |
| | Incisal | 70.73 | −1.34 | 15.58 | |

These results confirmed that the zirconia sintered bodies obtained by using a production method of the present invention are suited as dental products (for example, dental prostheses) because of the reduced stripes between layers having different yttria contents, despite a short firing time. It was also confirmed that the zirconia sintered bodies obtained by using a production method of the present invention can reproduce the shade and strength comparable to those of a dental prosthesis fired under normal conditions (total hours of firing: 6 to 12 hours), despite that the zirconia sintered bodies are sintered in a short time period.

INDUSTRIAL APPLICABILITY

A method of production of a zirconia sintered body of the present invention sinters a zirconia molded body or zirconia pre-sintered body in a short time period, and can reduce generation of stripes between layers having different yttria contents in the zirconia sintered body obtained. This makes a method of production of a zirconia sintered body of the present invention useful for the production of dental products (such as dental prostheses). A method of production of a zirconia sintered body of the present invention is also useful as a method of producing a dental prosthesis such as a post crown for front teeth because the zirconia sintered body produced can satisfy the aesthetics requirements (shade and translucency) as a dental prosthesis and reproduce strength as ideally as when fired under normal firing conditions, in addition to being particularly superior in shade, and having translucency comparable to that in the incisal edge portion of a natural front tooth, despite short sintering.

| 10 | Zirconia pre-sintered body |
|---|---|
| P | One end |
| Q | Other end |
| L | Entire length |
| Y | First direction |

The invention claimed is:

1. A method for producing a zirconia sintered body, comprising:
   firing a zirconia molded body or a zirconia pre-sintered body;
   wherein:
   the zirconia molded body or the zirconia pre-sintered body comprises a plurality of layers containing a stabilizer;
   the plurality of layers including layers have different stabilizer contents;
   firing comprises continuously increasing or retaining temperature through at least three stages comprising a first temperature-increasing stage (H1), a second temperature-increasing stage (H2), and a third temperature-increasing stage (H3);
   the method satisfies HR2=more than 0° C./min and less than 50° C./min, HR3=5° C./min or more and 150° C./min or less, and HR3/HR2>1, where HR2 is a rate of temperature increase in the second temperature-increasing stage (H2), and HR3 is a rate of temperature increase in the third temperature-increasing stage (H3);
   start temperatures of the temperature-increasing stages are 1,000° C. or less in H1, more than 1,250° C. and 1,450° C. or less in H2, and 1,450° C. or more and 1,550° C. or less in H3; and
   end temperatures of the temperature-increasing stages are more than 1,250° C. and 1,450° C. or less in H1, 1,450° C. or more and 1,550° C. or less in H2, and 1,500° C. or more and 1,750° C. or less in H3.

2. The method for producing a zirconia sintered body according to claim 1, wherein HR1 is 40 to 500° C./min, where HR1 is a rate of temperature increase in the first temperature-increasing stage (H1).

3. The method for producing a zirconia sintered body according to claim 1, wherein the stabilizer contents in the layers having different stabilizer contents differ by 0.1 mol % or more from one another.

4. The method for producing a zirconia sintered body according to claim 1, wherein the stabilizer is yttria.

5. The method for producing a zirconia sintered body according to claim 4, wherein a content of the yttria relative to total moles of the zirconia and the yttria is 2.5 mol % or more and 7.5 mol % or less in all of the layers in the plurality of layers.

6. The method for producing a zirconia sintered body according to claim 1, wherein HR2 is 2 to 30° C./min.

7. The method for producing a zirconia sintered body according to claim 1, wherein HR3 is 10 to 100° C./min.

8. The method for producing a zirconia sintered body according to claim 1, wherein HR3/HR2>1.5.

9. The method for producing a zirconia sintered body according to claim 1, wherein: firing comprises firing at a highest firing temperature of 1,400 to 1,750° C., and retaining the highest firing temperature for 30 minutes or less.

10. The method for producing a zirconia sintered body according to claim 9, wherein firing further comprises a temperature-decreasing in which temperature is decreased at a rate of 10° C./min or more from a highest firing temperature of the temperature-increasing stages to 800° C.

11. The method for producing a zirconia sintered body according to claim 1, wherein firing comprises firing for a total firing time of 120 minutes or less from a start of first temperature-increasing stage (H1) to an end of a retention time at a highest firing temperature.

12. The method for producing a zirconia sintered body according to claim 1, wherein 55% or more of the zirconia molded body or the zirconia pre-sintered body are monoclinic in crystal system.

13. The method for producing a zirconia sintered body according to claim 1, wherein at least a part of the stabilizer is not dissolved in zirconia as a solid solution in the zirconia molded body or the zirconia pre-sintered body.

14. The method for producing a zirconia sintered body according to claim 1, wherein the zirconia molded body or the zirconia pre-sintered body has a predetermined shape of a dental product.

15. The method for producing a zirconia sintered body according to claim 14, wherein the dental product is a dental prosthesis.

\* \* \* \* \*